United States Patent [19]

Kim et al.

[11] Patent Number: 5,441,725

[45] Date of Patent: *Aug. 15, 1995

[54] COSMETIC COMPOSITIONS CONTAINING A POLYETHOXYLATED VITAMIN E

[75] Inventors: Young D. Kim; Chang K. Kim; Choong N. Lee; Byung J. Ha, all of Seoul, Rep. of Korea

[73] Assignee: Pacific Corporation, Seoul, Rep. of Korea

[*] Notice: The portion of the term of this patent subsequent to Aug. 10, 2010 has been disclaimed.

[21] Appl. No.: 948,004

[22] Filed: Sep. 21, 1992

[30] Foreign Application Priority Data

Apr. 14, 1992 [KR] Rep. of Korea ................ 6157/1992

[51] Int. Cl.$^6$ .................... A61K 71/42; A61K 7/06
[52] U.S. Cl. .................... 424/59; 424/70.1; 514/458; 514/845; 514/846; 514/847; 514/848
[58] Field of Search ............ 424/401, 70; 514/458, 514/457, 456, 845, 846, 847, 848; 549/410, 412

[56] References Cited

U.S. PATENT DOCUMENTS

| | | | |
|---|---|---|---|
| 3,789,086 | 1/1974 | Frick | 549/410 |
| 3,883,565 | 5/1975 | Mulholland | 549/410 |
| 4,039,559 | 8/1977 | Nakamura | 549/410 |
| 4,347,256 | 8/1982 | Bowers | 549/410 |
| 4,760,095 | 7/1988 | Dierassi | 514/458 |
| 4,938,960 | 7/1990 | Ismail | 514/458 |
| 4,954,332 | 9/1990 | Bissett | 424/70 |
| 5,102,659 | 4/1992 | Hudson | 514/458 |
| 5,114,716 | 5/1992 | N'Guyen | 424/76.1 |
| 5,235,073 | 8/1993 | Kim | 549/408 |

FOREIGN PATENT DOCUMENTS

| | | |
|---|---|---|
| 0026546 | 4/1981 | European Pat. Off. . |
| 0082569 | 6/1983 | European Pat. Off. . |
| 0090445 | 10/1983 | European Pat. Off. . |
| 0092256 | 10/1983 | European Pat. Off. . |
| 1143372 | 7/1986 | Japan . |

OTHER PUBLICATIONS

G. J. Stockburger, *J. Am Oil Chemists' Soc.*, 56: 774A–777A, 1979.
J. A. Faucher et al., *J. Am Oil Chemist's Soc.*, 56: 776–782, 1989.
Y. C. Chiu et al., *Colloids and Surfaces*, 63: 311–322, 1992.
M. R. Davis, *Cosmetics & Toiletries*, 95: 87–92, 1980.
C. H. Fisher, *J. Am Oil Chemist's Soc.*, 56: 918–920, 1979.

Primary Examiner—G. S. Kishore
Assistant Examiner—Sally Garlner
Attorney, Agent, or Firm—Foley & Lardner

[57] ABSTRACT

The present invention relates to cosmetic compositions containing at least one polyethoxylated vitamin E species, which may be prepared by reacting a vitamin E with ethylene oxide, and exhibit an excellent cell protecting activity in the living body. The cosmetic compositions in the form of a skin-care, hair-care, lip-care and make-up cosmetic composition, which contain at least one polyethoxylated vitamin E species in an amount of 0.01 to 50% by weight, provide a protection against harmful oxygen species, show a moisture retention ability, and increase the tensile strength of hair, and substantivity and durability of the cosmetic compositions, when applied to the skin or hair.

21 Claims, 2 Drawing Sheets

FIG. 2

COSMETIC COMPOSITIONS CONTAINING A POLYETHOXYLATED VITAMIN E

BACKGROUND OF THE INVENTION

1. Filed of the Invention

The present invention relates to cosmetic compositions containing a polyethoxylated vitamin E. More particularly, it relates to cosmetic compositions containing a polyethoxylated vitamin E prepared by reacting vitamin E with ethylene oxide, which show a protective effect on cell membrane, a moisture retention ability and high safety.

2. Description of the Prior Art

Vitamin E is the generic name of a mixture of lipid soluble phenols, tocopherols and tocotrienols possessing general structural features: an aromatic chromanol head and a 16-carbon hydrocarbon tail. The number of methyl substituents in the chromanol nucleus gives rise to $\alpha$, $\beta$, $\gamma$, $\delta$ isomers, whereas the saturation of the hydrocarbon chain differentiates tocopherols with a saturated chain from tocotrienols with an unsaturated chain as forms of vitamin E. Tocopherols may be used for the purpose of blood capillary expansion, blood circulation promotion and skin moisturization as well as for preventing skin aging and alleviating frostbite. Further, it may effectively prevent the pigment deposition in the skin [See. Seok Man KIM, "Cosmetics Chemistry" published by Namsan Dang, p 70 (1976)]. When tocopherol is added to cosmetics, it moists the skin, provides the skin with elasticity, maitains the integrity of the skin and keeps the skin looking their best.

Tocopherols including tocopheryl acetate, tocopheryl succinate, tocopheryl nicotinate and the like have been used in cosmetic compositions. The cosmetic compositions containing tocopherols have been known to smooth the skin and protect the skin from the sun-light and aging.

However, although having these excellent properties, tocopherols are limited in their uses in cosmetic compositions because they are sensitive to oxidations by air and ultra vilolet ray [See. Maison G. deNavarre, "The Chemistry and Manufacture of Cosmetics", Continental Press, Vol. 2, 1962 p340–341]. Moreover, tocopherols used in the cosmetic compositions never sufficiently and stably exhibit their excellent properties.

Besides, the skin cell continually generates various free oxygen radicals, most of which are scavenged through protection mechanisms in the living body. But, a part of them attack unsaturated fatty acids in the biomembranes to form lipid superoxides. As a man age, the more lipid superoxides are formed and thus the aging is promoted. Among free oxygen radicals, particularly singlet oxygen has been found that it directly induces cell damages [See. R. M. Tyrrell, Photochem. Photobiol.) 49(4), 407–412, 1989]. Therefore, there has been a need for functional cosmetic compositions, which can provide a protection against harmful oxygen species.

SUMMARY OF THE INVENTION

An objective of the present invention is to provide a cosmetic composition which comprises a polyethoxylated vitamin E having the formula(I):

wherein,
R is $-(CH_2CH_2O)_nH$,
n is an integer from 2 to 100, inclusive,
A is

B is $-CH_3$ at the 5-, 7- or 8-position, and
m is 1, 2 or 3.

Another objective of the present invention is to provide a cosmetic composition which provide the skin and hair with a protection against harmful oxygen species and keep them looking their best, which comprises a polyethoxylated vitamin E of the formula(I) in an amount of 0.01 to 50% by weight.

Another objective of the present invention is to provide a cosmetic composition which comprises a polyethoxylated vitamin E in combination with tocopherol or tocopheryl ester.

Another objective of the present invention is to provide a method for protecting the skin and hair from the harmful oxygen species and keeping them looking their best, which comprises applying a cosmetic composition containing a polyethoxylated vitamin E in combination with or without tocopherol or tocopheryl ester, in an amount of 0.01 to 50% by weight, to the skin.

Other objects, advantages and features of the present invention will also become apparent to those skilled in the art from the following description.

DETAILED DESCRIPTION OF THE INVENTION

The present inventors have conducted extensive studies to find out vitamin E derivatives, which can be stably used in the cosmetic compositions and provide a protection against harmful oxygen species. As a result, we found that the above objective can be accomplished by polyethoxylated vitamin E species, particularly polyethoxylate vitamin E species having 2 to 100 moles of ethylene oxide in the molecule. The present inventors also found that the use of a polyethoxylated vitamin E in combination with tocopherol or tocopheryl ester may provide a superior protection against harmful oxygen species than the use of polyethoxylated vitamin E only. This synergic effect is attained, presumably, because the surface activity of the polyethoxylated vitamin E increases the absorption of tocopherol through the biomembrane and the polyethoxylated vitamin E helps tocopherol to scavenge more effectively harmful oxygen species.

Polyethoxylated vitamin E species of the present invention retain vitamin E's properties such as anti-oxidation and cell-protecting activities as well as show a good compatibility with other components of the cosmetic bases and increase their substantivity with the skin. The good properties of polyethoxylated vitamin E species as a component of cosmetic compositions are as follows: (1) they are very soluble in alcohols, (2) they have a high moisture retention ability, (3) they improve the durability of perfume components in the cosmetic compositions and inhibit vaporization of volatile components and (4) when applied to the skin, they give no sticky feel. These properties of polyethoxylated vitamin E species make it possible to use advantageously them in various cosmetic compositions, for example skin-care, hair-care, lip-care and make-up cosmetic compositions.

The present invention will be described in detail hereinafter.

Polyethoxylated vitamin E species used in the invention have the formula (I):

wherein,

R is $-(CH_2CH_2O)_{\overline{n}}H$, n is an integer from 2 to 100, inclusive,

A is

B is $-CH_3$ at the 5-, 7- or 8-position, and m is 1, 2 or 3.

Polyethoxylated vitamin E species may by prepared by reacting vitamin E witch ethylene oxides in accordance with the method described in, for example, U.S. Ser. No. 7-857652 filed by the present inventors on Mar. 26, 1992, which has matured into U.S. Pat. No. 5,235,073 the disclosure of which is hereby incorporated in their entirety by reference. They may be prepared by reacting vitamin E with ethylene oxide in the presence of basic catalyst or Lewis acid, preferably under pressure and in the absence of moisture. Vitamin E may include natural or synthetic α-, β-, γ- and δ-tocopherol and α-, β-, γ- and δ-tocotrienol.

Preferred polyethoxylated vitamin E species used in the invention are polyoxyethylene tocopheryl ester and isomers thereof.

Polyethoxylated vitamin E species provide an effective protection against active harmful oxygens and exhibit a moisture retention ability and safety in the living body.

Cosmetic compositions containing a polyethoxylated vitamin E may be present in the form of, not intended to be limited thereto, skin-care cosmetic compositions, hair-care cosmetic compositions, lip-care cosmetic compositions and make-up cosmetic compositions. The skin-care cosmetic compositions may include, for example, skin softners, toilet waters, astringents, facial creams, lotions, skin lotions, body lotions, cleansing creams, cleansing lotions, hand lotions, sun-screening creams, sun-screening lotions, essences, facial packs, massage creams and oil formulations. The hair-care cosmetic compositions may include, for example, shampoos, hair-rinses, hair-treatment creams, hair-styling mousses, hair-styling gels, hair sprays, hair tonics and hair pomades. The lip-care cosmetic compositions may include, for example, lipsticks, lip glosses and lip creams, and the makeup cosmetic compositions may include, for example, foundations and make-up bases.

The amount of polyethoxylated vitamin E species added in the cosmetic compositions may range from 0.01 to 50% by weight. Preferably, the skin-care and hair-care cosmetic compositions contain 0.01 to 30% by weight of, the lip-care cosmetic composition contains 0.01 to 30% by weight of and the make-up cosmetic composition contains 0.01 to 50% by weight of polyethoxylated vitamin E species.

Polyethoxylated vitamin E species show different functions depending on the number of moles of ethylene oxide added. For example, the polyethoxylated vitamin E having 2 to 7 moles of ethylene oxide in the molecule is an useful w/o emulsifier and disperses well inorganic pigments in an oil phase. That having 8 to 21 moles of ethylene oxide in the molecule is a good o/w emulsifier while that having 22 to 60 moles of ethylene oxide in the molecule shows a good gelation ability and disperses well inorganic pigments in an aqueous phase.

Thus, there may be selected polyethoxylated vitamin E having an appropriate number of moles of ethylene oxide in the molecule depending on the type and kind of the cosmetic compositions. For example, polyethoxylated vitamin E having 2 to 100 moles of ethylene oxide can be used for skin-care and make-up cosmetic compositions, that having 2 to 80 moles of ethylene oxide for hair-care cosmetic compositions and that having 2 to 10 moles of ethylene oxide for lip-care cosmetic compositions.

Cosmetic compositions according to the present invention may contain at least one species of the polyethoxylated vitamin E in combination with tocopherol or tocopheryl ester. The weight ratio of polyethoxylated vitamin species to tocopherol or tocopheryl ester is about 0.5:20 to 20:0.5, and preferably 2:3 to 3:2 for use in skin care cosmetic compositions and 1:10 to 10:1 for use in hair care cosmetic compositions.

The cosmetic compositions according to the invention which contain at least one species of the polyethoxylated vitamin E species in combination with or without tocopherol or tocopheryl ester exhibit an excellent cell protecting effect, a moisture retention ability and high safety in the living body. In case of the skin-care cosmetic compositions, they can screen the sun light.

When the hair-care cosmetic compositions containing polyethoxylated vitamin E species are applied to the hair, they increase the tensile strength of the hair and the hair is easy to comb out and glossy. Further, the make-up cosmetic compositions containing a polyethoxylated vitamin E species show a homogeneous pigment dispersion and provide a good color feel, substantivity and durability. Moreover, the cosmetic composition containing a polyethoxylated vitamin E has a good gelation ability so that they can be formulated into the gel-type cosmetics, which are currently on the market attracting public attention.

PREFERRED EMBODIMENT OF THE INVENTION

The present invention will be embodied by was of the following examples. However, these examples are provided for the illustration purpose only and should not be construed as limiting the scope of the invention, which is properly delineated in the accompanying claims.

Preparation 1

In a 1 $l$ double stainless steel autoclave were introduced 144 g of synthetic vitamin E (d $l$-α-tocopherol) and 0.2 g of KOH(purity 99.9%) and the moisture inside the reactor was removed by heating to 85° C. under vacuum of about 700 mmHg for 30 min. Then the relative pressure was adjusted to 0.1 kg/cm² with gaseous nitrogen followed by heating to 140° C.

45 g of ethylene oxide was slowly added thereto under the nitrogen atmosphere and the resulting mixture was reacted under stirring for about 4.5 hours. The pressure was adjusted to 4.8kg/cm² with gaseous nitrogen at the beginning of the reaction. As the reaction proceeded, the pressure became low until it kept constant at which the reaction was ended.

After completion of reaction, the reactor was degassed three times with gaseous nitrogen to remove unreacted ethylene oxide and by-produced 1,4-dioxane. The reaction mixture was cooled to about 12° C., at which it remains in the liquid state and a small amount of citric acid was added to neutralize the alkaline catalyst. The reaction mixture was purified by Sephadex LH-20 column chromatography using chloroform-methanol(1:1) to give 181 g of liquid polyethoxylated vitamin E.

(1) Appearance: liquid at room temperature
(2) Elemental Analysis: as a relative molecular weight of $C_{35}H_{61}O_5$

|  | C | H | N |
|---|---|---|---|
| Cal | 83.83 | 15.97 | 0.00 |
| Exp. | 84.65 | 15.20 | 0.05 |

(3) Yield: 96.1%
(4) Holes of ethylene oxide added: 3.0 at average (E.O.=3)

Preparation 2

In a 2 $l$ double stainless steel autoclave were introduced 200 g of synthetic vitamin E (d $l$-α-tocopheryl) acetate and 1.5 g of NaOH(purity 99.9%) and the moisture inside the reactor was removed by heating to 100° C. under vacuum of 0.05 kg/cm² for about 50 min.

1100 g of ethylene oxide was added thereto under the nitrogen atmosphere and the pressure was adjusted to 5.5 kg/cm² with gaseous nitrogen while heating to 150° C. After reaction for 8 hours under stirring, the reactor was degassed twice with gaseous nitrogen to remove unreacted ethylene oxide and by-produced 1,4-dioxane. The reaction mixture was cooled to 60° C., at which it remains in liquid state. The reaction mixture was treated with a small amount of citric acid to neutralize the alkaline catalyst and washed with benzene to remove unreacted vitamin E acetate. Then, the mixture was purified by Sephadex LH-20 column chromatography using methanol to give 365 g of solid polyethoxylated vitamin E.

(1) Melting Range: 56°-63° C.
(2) Elemental Analysis: as a relative molecular weight of $C_{129}H_{250}O_{52}$

|  | C | H | N |
|---|---|---|---|
| Cal. | 58.84 | 9.57 | 0.00 |
| Exp. | 58.49 | 9.81 | 0.05 |

(3) Yield: 96.15%
(4) Moles of ethylene oxide added: 51.2 at average (E.O.=51.2)

Example 1. Skin softner formulation

| | | |
|---|---|---|
| 1. | Butylene glycol | 1.0 part by weight |
| 2. | Glycerin | 2.0 |
| 3. | Sodium hyaluronate | 0.1 |
| 4. | Disodium ethylenediaminetetraacetate | 0.01 |
| 5. | Citric acid | 0.01 |
| 6. | Ethanol | 10.0 |
| 7. | Methyl paraoxybenzoate | 0.1 |
| 8. | Tocopherol | 0.03 |
| 9. | Polyoxyethylene (18) tocopheryl ether | 0.2 |
| 10. | Polyoxyethylene (12) nonylphenyl ether | 0.1 |
| 11. | Perfume | q.s. |
| 12. | Distilled water | to 100 |

Materials 1 to 5 were dissolved in material 12 and materials 7 to 11 were dissolved in material 6. Thus obtained two solutions were combined together, stirred and filtered.

Example 2. Cosmetic cream formulation

| | | |
|---|---|---|
| 1. | Cetostearyl alcohol | 3.0 part by weight |
| 2. | Stearic acid | 1.5 |
| 3. | Glyceryl monostearate | 3.0 |
| 4. | Squalane | 15.0 |
| 5. | Silicone oil | 0.5 |
| 6. | Lanolin | 5.0 |
| 7. | Polyoxyethylene (10) tocopheryl ether | 2.0 |
| 8. | Polyoxyethylene (20) sorbitan monostearate | 0.5 |
| 9. | Propyl paraoxybenzoate | 0.2 |
| 10. | Methyl paraoxybenzoate | 0.2 |
| 11. | Triethanolamine | 0.2 |
| 12. | Glycerin | 5.0 |
| 13. | Sodium hyaluronate | 0.01 |
| 14. | Placenta extract | 0.2 |
| 15. | Perfume | q.s. |
| 16. | Colorant | q.s. |
| 17. | Distilled water | to 100 |

Material 13 was dispersed into material 17, to which materials 1 to 12, 14 and 15 were added to give an aqueous phase. Materials 17 and 19 were dissolved in material 16 to give an alcoholic phase. The alcoholic phase was added gradually to the aqueous phase under stirring, to which material 18 was added.

Example 3. Lotion formulation

| | | |
|---|---|---|
| 1. | Cetostearyl alcohol | 1.0 part by weight |
| 2. | Stearic acid | 0.5 |
| 3. | Glyceryl monostearate | 0.5 |
| 4. | Squalane | 10.0 |
| 5. | Polyoxyethylene (12) tocopheryl ether | 0.5 |
| 6. | Polyoxyethylene (20) sorbitan monostearate | 1.5 |
| 7. | Sorbitan sesquioleate | 0.5 |
| 8. | Methyl paraoxybenzoate | 0.2 |
| 9. | Propyl paraoxybenzoate | 0.1 |

-continued

| 10. | Triethanolamine | 0.1 |
| 11. | Carboxyvinyl polymer | 0.1 |
| 12. | Perfume | q.s. |
| 13. | Colorant | q.s. |
| 14. | Distilled water | to 100 |

Materials 1 to 4 were melted by heating to 75° C. to give an oil phase, Materials 10 and 11 were dissolved in material 14, to which materials 5 to 9 were added. The aqueous phase was heated to 75° C. and mixed With the oil phase. The mixture was cooled to 50° C. and materials 12 and 13 were added thereto. The mixture was stirred and cooled to room temperature, Example 4. Body lotion formulation

| 1. | PEG-7 hydrogenated caster oil | 6.0 part by weight |
| 2. | Microcrystalline wax | 2.0 |
| 3. | Caprylic/capric triglyceride | 5.0 |
| 4. | Polyoxyethylene (20) sorbitantrioleate | 1.0 |
| 5. | Polyoxygethylene (15) tocopheryl ether | 2.0 |
| 6. | Tocopherol | 1.5 |
| 7. | Magnesium sulfate | 0.7 |
| 8. | Panthenol | 2.0 |
| 9. | Perfume | q.s. |
| 10. | Colorant | q.s. |
| 11. | Preservative | q.s. |
| 12. | Distilled water | to 100 |

Materials 1 to 6 were melted by heating to 75° C. to give an oil phase. Materials 7 and 8 were dissolved in material 12 and heated to 75 ° C. The aqueous phase were mixed with the oil phase and cooled to 50° C. Materials 9 to 11 were added and the mixture was stirred and cooled to room temperature.

Example 5. Sun-screening emulsion formulation

| 1. | Polyoxyethylene (3) tocopheryl ether | 10.0 part by weight |
| 2. | Tocopherol | 4.0 |
| 3. | Ceteareth-6 and stearyl alcohol | 2.0 |
| 4. | Ceteareth-25 | 1.0 |
| 5. | Cetyl alcohol | 1.0 |
| 6. | Glyceryl monostearate | 6.0 |
| 7. | Paraffin oil | 5.0 |
| 8. | Capric/Caprylic triglyceride | 5.0 |
| 9. | Propylene glycol | 3.0 |
| 10. | Titanium dioxide | 2.0 |
| 11. | Silicone oil | 0.2 |
| 12. | Preservative | q.s. |
| 13. | Perfume | q.s. |
| 14. | Distilled water | to 100 |

Materials 1 to 3 and 5 to 8 were melted by heating to 75° C. to give an oil phase. Materials 4 and 9 were added to material 14 and melted at 75° C., into which material 10 was dispersed. The mixture was combined with oil phase and cooled to 50° C. Materials 11 to 13 were added and the mixture was stirred and cooled to room temperature.

Examples 6 to 8 and Comparison Examples 1 to 2

Hair shampoo formulations (Unit: part by weight)

| Material | Ex. 6 | Ex. 7 | Ex. 8 | Comparison Ex. 1 | Comparison Ex. 2 |
|---|---|---|---|---|---|
| 1. Polyoxyethylene (18) tocopheryl ether | 0.2 | 0.1 | 0.1 | — | — |
| 2. Tocopherol | — | 0.1 | — | 0.2 | — |
| 3. Tocopheryl acetate | — | — | 0.1 | — | 0.2 |
| 4. Sodium laurylsulfate (30%) | 40.0 | 40.0 | 40.0 | 40.0 | 40.0 |
| 5. Cocoampocarboxypropionate (70%) | 10.0 | 10.0 | 10.0 | 10.0 | 10.0 |
| 6. Laurylmyristoyl D.E.A. | 5.0 | 5.0 | 5.0 | 5.0 | 5.0 |
| 7. Propylene glycol | 1.0 | 1.0 | 1.0 | 1.0 | 1.0 |
| 8. Preservative | q.s. | q.s. | q.s. | q.s. | q.s. |
| 9. Colorant | q.s. | q.s. | q.s. | q.s. | q.s. |
| 10. Perfume | q.s. | q.s. | q.s. | q.s. | q.s. |
| 11. Distilled water | to 100 | 100 | 100 | 100 | 100 |

Materials 1 to 8 were added to material 11 and the mixture was melted at 70° C. and then cooled to 55° C. Materials 9 and 10 were added and the mixture was stirred and cooled to room temperature.

Example 9. Hair rinse formulation

| 1. | Cetyl alcohol | 1.0 part by weight |
| 2. | Glycerin monostearate | 1.0 |
| 3. | Hydroxyethyl cellulose | 2.0 |
| 4. | Propyleneglycol | 4.0 |
| 5. | Methyl paraoxybenzoate | 0.2 |
| 6. | Stearyl alcohol | 2.0 |
| 7. | Perfume | q.s. |
| 8. | Citric acid | q.s. |
| 9. | Colorant | q.s. |
| 10. | Polyoxyethylene (12) tocopheryl ether | 0.1 |
| 11. | Tocopheryl acetate | 0.1 |
| 12. | Disodium ethylenediaminetetraacetate | 0.05 |
| 13. | Distilled water | to 100 |

Materials 1 to 6 were heated to 75° C. and added to material 13 which was heated to 75° C. Materials 8 to 12 were added to the emulsion, and it was cooled to 50° C. Material 7 was added, and the mixture was stirred and cooled to room temperature.

Example 10. Hair treatment cream formulation

| 1. | Polyoxyethylene (25) lanolin alcohol | 2.0 part by weight |
| 2. | Isopropyl myristate | 3.0 |
| 3. | Methyl paraoxybenzoate | 0.2 |
| 4. | Monostearic glycerin | 3.0 |
| 5. | Cetyl alcohol | 5.5 |
| 6. | Polyoxyethylene (10) tocopheryl ether | 0.6 |
| 7. | Perfume | q.s. |
| 8. | Colorant | q.s. |
| 9. | Distilled water | to 100 |

Materials 1 to 5 were melted by heating to 70°–75° C. and added to materials 6, 8 and 9 which were heated to 70°–75° C. The mixture was stirred and emulsified with material 7, and cooled to room temperature.

Example 11. Hair spray(Non-aerosole type) formulation

| 1. | Polyvinylpyrrolidonevinylacetate | 3.0 part by weight |

-continued

|   | | |
|---|---|---|
|   | copolymer | |
| 2. | Polyquaternium-11 | 1.0 |
| 3. | Olealconium chloride | 0.3 |
| 4. | PEG(40) castor oil | 0.15 |
| 5. | Polyoxyethylene (15) tocopheryl ether | 0.05 |
| 6. | Tocopherol | 0.05 |
| 7. | Ethanol | to 100 |

Materials 1 to 6 were successively dissolved in material 7.

Example 12 and Comparison Example 3. Lipstick formulations

|   | Material | Ex. 12 | Comparison Ex. 3 |
|---|---|---|---|
| 1. | Castor oil | to 100 | 100 part by weight |
| 2. | Wood wax | 5.0 | 5.0 |
| 3. | Hydrogenated castor oil | 4.0 | 4.0 |
| 4. | Cetostearyl alcohol | 3.0 | 3.0 |
| 5. | Paraffin | 2.0 | 2.0 |
| 8. | Liquid paraffin | 10.0 | 10.0 |
| 7. | Liquid lanolin | 11.0 | 11.0 |
| 8. | Sorbitan sesquioleate | — | 1.0 |
| 9. | Polyoxyethylene (2) tocopheryl ether | 1.0 | — |
| 10. | Mica titanium | 8.0 | 8.0 |
| 11. | Ferric oxide | 0.2 | 0.2 |
| 12. | Calcium lake Red No. 202 | 0.3 | 0.3 |
| 13. | Antioxidant | 0.1 | 0.1 |
| 14. | Perfume | 0.2 | 0.2 |

Materials 1 to 9 were melted by heating to 80° C., into which materials 10 to 12 were dispersed. The dispersion was degassed and materials 13 and 14 were added thereto. The mixture was cooled to 30° C.

Example 13. Lip cream formulation

|   |   |   |
|---|---|---|
| 1. | Castor oil | to 100 part by weight |
| 2. | Canderilla wax | 3.0 |
| 3. | Wood wax | 2.0 |
| 4. | Hydrogenated castor oil | 2.0 |
| 5. | Liquid paraffin | 5.0 |
| 6. | Polybutene | 30.0 |
| 7. | Lanolin | 10.0 |
| 8. | Polyoxyethylene (5) tocopheryl ether | 1.5 |
| 9. | Mica titanium | 0.5 |
| 10. | Yellow ferric oxide | 0.1 |
| 11. | Aluminium lake Yellow No. 4 | 0.15 |
| 12. | Antioxidant | 0.1 |
| 13. | Perfume | 0.2 |

Materials 1 to 9 were melted by heating to 80° C. and materials 10 to 12 were dispersed therein. The dispersion was degassed, materials 13 and 14 were added thereto and the mixture was cooled to 30° C.

Example 14 and Comparison Example 4. Facial emulsion foundation formulations

|   | Material | Ex. 14 | Comparison Ex. 4 |
|---|---|---|---|
| 1. | Volatile silicone | to 100 | 100 part by weight |
| 2. | Liquid paraffin | 10.0 | 10.0 |
| 3. | Sesquioleic sorbitan | — | 3.0 |
| 4. | Polyoxyethylene (5) tocopheryl ether | 3.0 | — |
| 5. | Microcrystalline wax | 2.0 | 2.0 |
| 6. | Bee wax | 3.0 | 3.0 |
| 7. | Paraffin | 3.0 | 3.0 |
| 8. | Aluminium stearate | 0.3 | 0.3 |
| 9. | Preservative | 0.2 | 0.2 |
| 10. | Titanium dioxide | 9.5 | 9.5 |
| 11. | Talc | 3.1 | 3.1 |
| 12. | Ferric oxide | 0.9 | 0.9 |
| 13. | Yellow ferric oxide | 1.4 | 1.4 |
| 14. | Black ferric oxide | 0.2 | 0.2 |
| 15. | Distilled water | 45.0 | 45.0 |
| 16. | Glycerin | 3.0 | 3.0 |
| 17. | Magnesium sulfate | 0.4 | 0.4 |
| 18. | Perfume | 0.3 | 0.3 |

Materials 1 to 9 were melted by heating to 80° C., into which materials 10 to 14 were dispersed, Materials 15 to 17 were added gradually under heating to 80° C. and the mixture was stirred for 30 min. After adding material 18, the mixture was stirred and cooled to 30° C.

Example 15. Make-up base emulsion formulation

|   |   |   |
|---|---|---|
| 1. | Distilled water | to 100 part by weight |
| 2. | Triethanolamine stearate | 1.0 |
| 3. | Propylene glycol | 4.0 |
| 4. | Triethanolamine | 0.9 |
| 5. | Bentonite | 1.2 |
| 6. | Chromium oxide | 1.1 |
| 7. | Titanium dioxide | 3.0 |
| 8. | Talc | 3.9 |
| 9. | Cethanol | 0.7 |
| 10. | Stearic acid | 2.0 |
| 11. | Liquid paraffin | 19.0 |
| 12. | Bee wax | 1.0 |
| 13. | Sesquioleic sorbitan | 1.0 |
| 14. | Polyoxyethylene (21) tocopheryl ether | 1.2 |
| 15. | Preservative | 0.2 |
| 16. | Perfume | 0.2 |

Materials 1 to 5 were melted by heating to 70° C. and mixed with materials 6 to 8. Materials 9 to 16 were heated to 80° C and added to the above mixture which was heated to 73° C. The mixture was stirred and cooled to 30° C.

Example 16. Make-up base gel formulation

|   |   |   |
|---|---|---|
| 1. | Distilled water | to 100 part by weight |
| 2. | Ethanol | 5.0 |
| 3. | Glycerin | 5.0 |
| 4. | Propylene glycol | 2.0 |
| 5. | Xanthan gum | 0.2 |
| 6. | Carboxyvinyl polymer | 0.4 |
| 7. | Methyl paraoxybenzoate | 0.15 |
| 8. | Perfume | 0.1 |
| 9. | Hohoba oil | 0.2 |
| 10. | Polyvinylpyrrolidone | 0.4 |
| 11. | Polyoxyethylene (50) tocopherol ether | 15.0 |
| 12. | Triethanolamine | 0.45 |

Materials 5 and 6 were dissolved in materials 1 to 4 with stirring. Materials 7 to 11 were added under stirring and it was neutralized by adding material 12.

Experimental Example 1. Oxidative stability of polyethoxylated vitamin E

The OH group at the 6-position of vitamin E is susceptible to oxidation by air, light or UV and has a strong reducing ability. Its oxidation is accelerated by the presence of an inorganic salt such as a ferric salt while it shows a considerable stability against heat and alkali. However, when the OH at the 6-position is esterified, the tocopherol is not easily oxidized but it is unstable under alkaline conditions and the unstability is increased by heat.

In order to examine the oxidative stability of polyethoxylated vitamin E species according to the present invention, their reducing ability was determined using decoloration of methylene blue by the method described in Japanese Patent No Sho 53-2775.

100 mg of each vitamin E, vitamin E acetate or polyethoxylated vitamin E prepared in Example 1 was placed in a test tube and 100 ml of purified water was added thereto. The solution was made weakly alkaline with sodium hydroxide, heated to 60° C. and 10 ml aqueous 0.1% methylene blue solution was added thereto.

The vitamin E solution began to be decolorized after 15 minuted and was totally decolorized after about 1 hour. Thus, tocopherol has a considerable reducing ability.

The vitamin E acetate solution was totally decolorized after about 80 hours while the polyethoxylated vitamin E solution was totally decolorized after about 85 hours. Therefore, polyethoxylated vitamin E has some oxidative stability which is similar to that of vitamin E acetate.

Experimental Example 2: Cell protecting action of cosmetic compositions containing polyethoxylated vitamin E In order to examine the cell protecting action of polyethoxylated vitamin E species, a photochemolysis test was carried out by using the following three cosmetic compositions shown in Table 1 as described below [See. S-N Park, D-H Lee, T-Y Lee, J. Soc, Cos. Chemists (Korea), 13 45(1987)]:

TABLE 1

| Materials | Conventional | (Unit: % by weight) Invention 1 | Invention 2 |
|---|---|---|---|
| 1. Glycerin | 2.0 | 2.0 | 2.0 |
| 2. Disodium ethylenediaminetetracetate | 0.01 | 0.01 | 0.01 |
| 3. Methyl paraoxybenzoate | 0.1 | 0.1 | 0.1 |
| 4. Ethanol | 10.0 | 10.0 | 10.0 |
| 5. Polyoxyethylene nonylphenyl ether | 0.2 | — | — |
| 6. Perfume | 0.1 | 0.1 | 0.1 |
| 7. Polyoxyethylene (10) tocopheryl ether | — | 0.2 | 0.2 |
| 8. Tocopherol | — | — | 0.15 |
| 9. Distilled water | to 100 | 100 | 100 |

Blood collected from a rabbit was centrifuged at 8000 rpm for 5 minutes and washed to obtain erythrocytes, which were diluted with physiological saline to give an erythrocyte suspension($6 \times 10^1$ erythrocytes/3.5 ml).

Four pyrex test tubes of 1.0 cm diameter were prepared and each was charged with 3.5 ml of the suspension. One of the four test tubes was taken as a control group, to which 50 ml of each sample was added. Four test tubes were preincubated in the dark for 30 minutes and the end of the test tubes was sealed with a paraffin film. In the center of a $50 \times 20 \times 25$ cm rectangular hexahedron box the inside of which had been painted a black color was placed a 20 W fluorescent lamp. The test tubes were located at points 5 cm distant from the lamp and were irradiated for 15 minutes.

After completion of irradiation, the transmittances of each test tube kept in the dark at 700 nm were measured at intervlas of 15 minutes. The increase in the transmittance of the suspension at this wavelength was proportional to the degree of hemolysis.

Every step of the above experiment was carried out in a constant temperature room at 27° C. The cell protecting activity of the sample against active oxygen species was defined as the time(min) required for hemolyzing 50% of the erythrocytes under the above measurement conditions. The results are shown in Table 2.

TABLE 2

| Cell protecting activity of polyethoxylated vitamin E-containing cosmetic compositions | |
|---|---|
| Sample | Cell protecting activity (min) |
| Control | 50 |
| Conventional | 70 |
| Invention 1 | 160 |
| Invention 2 | 180 |

As shown in the above Table 2, cosmetic compositions containing a polyethoxylated vitamin E according to the present invention show a strong activity of at least three times the control and two times the conventional cosmetic composition.

Experimental Example 3. Moisture retention effect of polyethoxylated vitamin E

The moisture retention ability of polyoxyethylene(12) tocopheryl ether was compared with those of glycerin, which is most commonly used as a humectant, pyrrolidone carboxylic acid sodium salt (PCA-Na) and polyoxyethylene(20) sorbitan monostearate.

Figure 1:
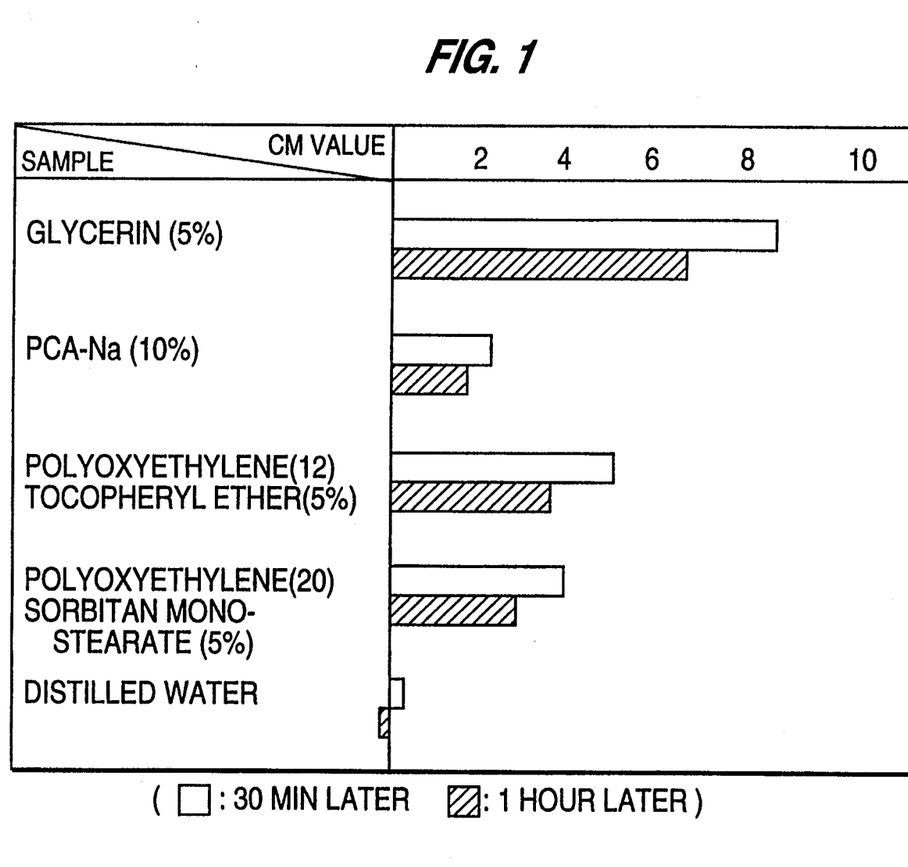
FIG. 1 shows the moisture retention ability of polyoxyethylene tocophenyl ether as compared to comparative compounds.

Solutions of test compounds and distilled water were applied to the skin of healthy volunteers. 30 min or 1 hour later, the hydrations were determined using Corneometer CM 820PC(Schwarzhaupt, Germany) and the results are shown in FIG. 1.

As shown in FIG. 1, the polyethoxylated Vitamin E species show a potent moisture retention ability and is very soluble in water, and thus may be effectively used as a humectant in cosmetics.

Example 4. Safety in the living body: Primary eye irritation test

In order to evaluate the safety of polyethoxylated vitamin E species of the present invention in the living body, the primary eye irritation test was carried out using a rabbit according to the Draize procedure [J. H. Draize, "Appraisal of the safety of chemicals in food, drug and cosmetics", Association of Food and Drug Officials of the U.S. Topeka 49( 1965)].

A test compound selected from polyoxyethylene(10) tocopheryl ether, polyoxyethylene (15) tocopheryl ether and polyoxyethylene (20) sorbitan monostearate was diluted with 10% aqueous glycerin solution to give 10% test samples.

Six healthy albino rabbits weighing 2 to 3 kg were chosen, and 0.1 ml of the test sample was dropped onto one eye of each rabbit, taking the other eye as a control. 24 hours later, the average scores were recorded according to the Draize scoring for ocular lesions. If lesions were present the time was extended.

Figure 2:
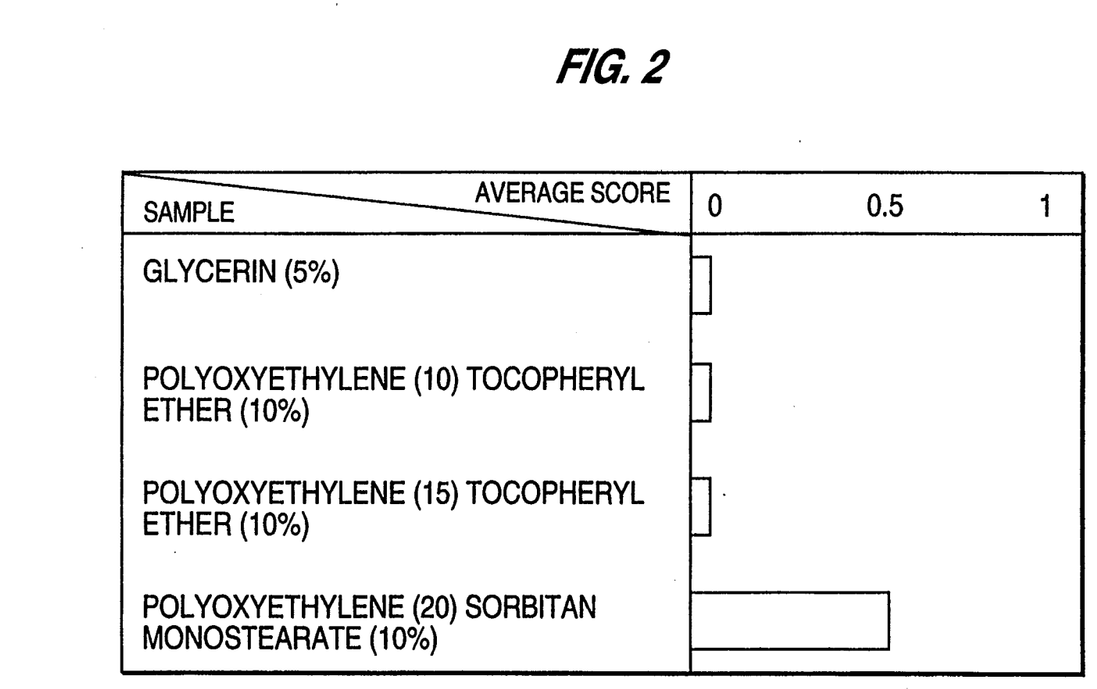
FIG. 2 shows the eye irritation of polyethoxylated vitamin E as compared to comparative compounds.

The results are shown in FIG. 2.

As shown in FIG. 2, the polyethoxylated vitamin E species of the present invention were weaker irritants than polyoxyethylene sorbitan monostearate. Therefore, cosmetic compositions containing a polyethoxylated vitamin E according to the present invention may be advantageously formulated into skin-care cosmetic compositions such as eye creams, hair-care cosmetic compositions such as shampoos or rinses and make-up cosmetic compositions such as foundations or lipsticks.

Experimental Example 5. UV light-screening activity

In order to evaluate the UV-light screening activity of polyethoxylated vitamin E species of the present invention, UV-absorption thereof was comparied with those of homosalate and tocopherol, which are conventionally used as a UV light-screening agent in cosmetics.

Test compounds were dissolved in ethanol to a concentration of 0.001% and their absorbances were measured by using a UV spectrophotometer. As a result, polyoxyethylene tocopheryl ether with 1 to 18 moles of ethylene oxide showed an UV-absorbing activity. Particularly, polyoxyethylene tocophery ether with 5 moles of ethylene oxide exhibited an UV-absorbing activity corresponding to about 75% of that of homosalate and tocopherol. Therefore, polyethoxylated vitamin E species can be used as a UV-absorbant in cosmetics for protecting skin from sun light.

Experimental Example 6. Effect of cosmetic compositions containing polyethoxylated vitamin E on the skin In order to evaluate the effect of skin-care cosmetic composition containing a polyethoxylated vitamin E on the skin, the conventional composition and the inventive composition 2 in Experimental Example 2 were estimated for the moisture retention ability, smooth and elsticity of the skin and the ability of alleviating the skin abnormality such as pimple.

30 females aging 20 to 30 having a pimpled face were applied the inventive composition 2 on the right side of the face and the convnetional composition on the left side of the face. After 5 hours, for assessing the test items, i.e., moisture retention ability, smooth and elasticity of the skin and the ability of alleviating the skin abnormality, the subject choose the preferred of the two compositions tested on the subject. The evalution was carried out for ten days in order to provide a reliability. For each effect, 1 point was given for the chosen shampoo and 0 for the other by each subject and the average for ten days was taken. The results are shown in Table 5.

TABLE 5

| Sample | Test item | | | |
|---|---|---|---|---|
| | Moisture retention ability | Smoothness of skin | Elasticity of skin | Skin abnormality alleviating effect |
| Invention | 20 | 19 | 21 | 21 |
| Conventional | 10 | 11 | 9 | 9 |

Experimental Example 7. Tensile strength increase by polyethoxylated vitamin E

In order to evaluate the ability of increasing tensile strength of the hair, polyoxyethylene (18) tocopheryl ether at various concentrations of 1 to 5% and tocopherol as a control were tested for force reduction(%). The force reduction (%) was measured at 20°±2° C. and relative humidity of 60±4% by using Rheo Meter(-model 200-2J, Fudo Kogyo Co., Japan). Under the conditions of initial hair length 50 mm, the rate of extension was 5 cm/min and full scale was 200 gf.

The percentage reduction in force was calculated according to the following equation:

$$\text{Force reduction (\%)} = \frac{F_0 - F_1}{F_0} \times 100$$

where $F_0$ is the initial force required to extend a fiber 20% and $F_1$ is the force required to reextend the same fiber 20% after treatment [See. N. B. Fair and B. S. Gupta, The use of multiple test methods in the analysis of the effect of cosmetic treatment on the surface properties of human hair, XIVth IFSCC Congress, Barcelona, Vol II, pp 1113-1124 (1986)]. In this test, bleached hair was employed, which was treated with 6% (20 volume) aqeous hydrogen peroxide solution for 30 min and then immersed in the test sample soultion for 15 hours.

As a result, the force reduction by polyoxyethylene tocopheryl ether was lower 30% than that by tocopherol at 4% and 5% concentrations, while the former was similar to the latter at 1%, 2% and 3% concentrations.

Experimental Example 8. Effect of cosmetic composition containing polyethoxylated vitamin E on the hair In order to evaluate the effect of the cosmetic compositions containing a polyethoxylated vitamin E in combination with or without tocopherol and tocopheryl acetate on the hair, the half-head test was carried out by using shampoos in Examples 6 to 8 and Comparative Example 1 and 2 [See. C. Robbins "Chemical & Physical behavior of human hair", Von Nostrand Reinhold, New York, 102-110 (1979)].

The 50 female subjects were divided into 5 groups and the right and left sides of their hair were treated with the shampoos as shown in Table 6. The control shampoo used in the test has the same composition as the shampoo of Comparison Example 2 except that it contains no tocopheryl acetate. For assessment of the items in Table 6, the subject and operator choose the preferred of the two shampoos tested on the subject by evaluating the left and right parts of the subject's hair. The evaluation was carried out twice and the results are shown in Table 6.

TABLE 6

| Group No. | 1 | | 2 | | 3 | | 4 | | 5 | |
|---|---|---|---|---|---|---|---|---|---|---|
| Side of hair* | L | R | L | R | L | R | L | R | L | R |
| Shampoo in | Ex. 6 | Ex. 7 | Ex. 8 | Ex. 6 | Ex. 6 | Comp. Ex. 1 | Comp. Ex. 2 | Ex. 6 | Ex. 6 | Control |
| Wet hair | | | | | | | | | | |
| Feel | 9 | 11 | 10 | 10 | 12 | 8 | 10 | 10 | 11 | 9 |
| Easiness to comb | 8 | 12 | 11 | 9 | 11 | 9 | 7 | 13 | 16 | 4 |
| Dry hair | | | | | | | | | | |

TABLE 6-continued

| Group No. | 1 | | 2 | | 3 | | 4 | | 5 | |
|---|---|---|---|---|---|---|---|---|---|---|
| Side of hair* | L | R | L | R | L | R | L | R | L | R |
| Feel | 10 | 10 | 9 | 11 | 10 | 10 | 6 | 14 | 17 | 3 |
| Easiness to comb | 9 | 11 | 11 | 9 | 12 | 8 | 7 | 13 | 16 | 4 |
| Sheen | 10 | 10 | 9 | 11 | 11 | 9 | 5 | 15 | 18 | 2 |
| Antistatic effect | 11 | 9 | 11 | 9 | 12 | 8 | 4 | 16 | 16 | 4 |
| Wet hair total points | 17 | 23 | 21 | 19 | 23 | 17 | 17 | 23 | 27 | 13 |
| Dry hair total points | 40 | 40 | 40 | 40 | 45 | 35 | 22 | 58 | 67 | 13 |
| Total points | 57 | 63 | 61 | 59 | 68 | 52 | 39 | 81 | 94 | 26 |
| Preference (%) | 47 | 53 | 51 | 49 | 57 | 43 | 33 | 67 | 78 | 22 |

*Note:
L : Left side,
R : Right side

As shown in Table 6, shampoos in Examples 7 and 8, which contain polyoxyethylene tocopheryl ether in combination with tocopherol or tocopheryl ester got a slightly higher preference than shampoo in Example 6, which contains polyoxyethylated tocopheryl ether without tocopherol and tocopheryl ester. However, shampoos containing polyoxyethylene tocopheryl ether got a much higher preference than shampoos (Comparative Example 1 and 2) containing tocopherol or tocoperyl ester only. Further, shampoo of Example 6 got a preference of about 3.5 times that of control, which contain no polyoxyethylene tocopheryl ether, tocopherol and tocopheryl ester.

Experimental Example 9. Dispersing power of polyethoxylated vitamin E

The dispersing power, emulsifying power and emulsion stability of polyethoxylated vitamin E species were evaluated by using the lipsticks in Example 12 and Comparative Example 3 and the emulsion foundations in Example 14 and Comparative Example 4. The lipsticks were evaluated for the dispersing power and sweating phenomenon, and the emulsion foundations were evaluated for the dispersing power, emulsifying power and emulsion stability.

Pigment dispersion and emulsion conditions were observed with a polarization microscope and naked eyes at 30° C. Sweating was observed after standing the lipstick at 5° C. and 37° C. in twelve-hour shifts, and emulsion stability was observed with naked eyes after storing at 45° C. for 50 days. The results are shown in Table 7.

TABLE 7

| | Test item | | | |
|---|---|---|---|---|
| Sample | Dispersion | Emulsion | Sweating | Emulsion stability |
| Lipstick | | | | |
| Example 12 | Pigment is homogeneously | — | No | — |
| Comparative Example 3 | dispersed Pigment is not homogeneously dispersed, but coagulated | — | Sweating is occurred on the surface | — |
| Foundation | | | | |
| Example 14 | Pigment is homogeneously dispersed | Emulsion particles having a diameter of 1~2 μm are formed | — | No precipitation of the pigment |
| Comparative Example 4 | Pigment is not homogeneously dispersed, rather coagulated | Emulsion particles having a diameter of 1~6 μm are formed | — | Pigment is precipitated and supernatant is formed |

Experimental Example 10. Characteristics of make-up cosmetic compositions containing polyethoxylated vitamin E 30 females aging 20 to 30 years alternatively applied the two lipsticks in Example 12 and Comparative Example 3 to their lips and choose the preferred one in regard with terms of substantivity, durability and gloss. Besides, 50 females aging 20 to 30 years applied the foundation in Example 14 to the left side of their face and the foundation in Comparative Example 4 to the right side, and choose the preferred side in regard with terms of spreadability, substantivity, durability, and moistness and smoothness of the skin. The evaluation was carried out five thimes. For each effect, 1 point was given for the chosen cosmetic compositions and 0 for the otehr by each subject and the average for five runs was taken.

The results are shown in Table 8.

TABLE 8

| | Test item | | | | | |
|---|---|---|---|---|---|---|
| Sample | Spreadability | Substantivity | Durability | Gloss | Moistness of skin | Smoothness of skin |
| Lipstick | | | | | | |
| Ex. 12 | — | 25 | 26 | 24 | — | — |
| Comp. Ex. 3 | — | 5 | 4 | 6 | — | — |
| Foundation | | | | | | |
| Ex. 14 | 34 | 39 | 36 | — | 29 | 36 |

TABLE 8-continued

| Sample | Spreadability | Substantivity | Durability | Gloss | Moistness of skin | Smoothness of skin |
|---|---|---|---|---|---|---|
| Comp. Ex. 4 | 16 | 11 | 14 | — | 21 | 14 |

What is claimed is:

1. A cosmetic composition comprising a polyethoxylated vitamin E, which has the formula(I):

wherein,
R is $(CH_2CH_2O)_n$ H,
n is an integer from 2 to 100, inclusive,
A is

B is —$CH_3$ at the 5-, 7- or 8-position, and
m is 1, 2 or 3, in an amount of 0.01 to 50% by weight.

2. The cosmetic composition according to claim 1, wherein said polyethoxylated vitamin E is prepared by a process comprising the step of reacting a compound selected from the group consisting of natural tocopherol, synthetic tocopherol, and tocotrienol with ethylene oxide in the presence of a basic catalyst, under a pressure of 3.0 to 6.0 kg/cm$^2$ and at a temperature of 140° to 160° C.

3. The cosmetic composition according to claim 2, wherein said polyethoxylated vitamin E is a polyoxyethylene tocopheryl ether or an isomer thereof.

4. The cosmetic composition according to claim 1, which contains said polyethoxylated vitamin E in an amount of 0.01 to 50% by weight in combination with tocopherol or tocopheryl ester, and wherein the weight ratio of said polyethoxylated vitamin E to tocopherol or tocopheryl ester is 0.5:20 to 20:0.5.

5. The cosmetic composition according to claim 1, wherein the weight ratio of polyethoxylated vitamin E to tocopherol or tocopheryl ester is 10:1 to 1:10.

6. The cosmetic composition according to claim 1, which is a skin-care cosmetic composition selected from the group consisting of skin softners, astringents, facial creams, skin lotions, body lotions, cleansing creams, cleansing lotions, hand lotions, sun-screening creams, essences, facial packs, massage creams and oil formulations.

7. The cosmetic composition according to claim 6, wherein said skin-care cosmetic composition contains said polyethoxylated vitamin E in an amount of 0.01 to 30% by weight.

8. The cosmetic composition according to claim 7, wherein said skin-care cosmetic composition contains said polyethoxylated vitamin E in combination with tocopherol or tocopheryl ester, and wherein the weight ratio of said polyethoxylated vitamin E to tocopherol or tocopheryl ester is 0.5:20 to 20:0.5.

9. The cosmetic composition according to claim 1, which is a hair-care cosmetic composition selected from the group consisting of shampoos, hair rinses, hair treatment creams, hair styling mousses, hair styling gels, hair sprays, hair tonics and hair pomades.

10. The cosmetic composition according to claim 9, wherein said hair-care cosmetic composition contains said polyethoxylated vitamin E in an amount of 0.01 to 30% by weight.

11. The cosmetic composition according to claim 10, wherein said hair-care cosmetic composition contains said polyethoxylated vitamin E in combination with tocopherol or tocopheryl ester, and wherein the weight ratio of said polyethoxylated vitamin E to tocopherol or tocopheryl ester is 0.5:20 to 20:0.5.

12. The cosmetic composition according to claim 11, wherein said polyethoxylated vitamin E contains 2 to 80 moles of ethylene oxide in the molecule.

13. The cosmetic composition according to claim 1, which is a lip-care cosmetic composition selected from the group consisting of lipsticks, lip glosses and lip creams.

14. The cosmetic composition according to claim 13, wherein said lip-care cosmetic composition contains said polyethoxylated vitamin E in an amount of 0.01 to 20% by weight.

15. The cosmetic composition according to claim 13, wherein said polyethoxylated vitamin E contains 2 to 10 moles of ethylene oxide in the molecule.

16. The cosmetic composition according to claim 1, which is a make-up cosmetic composition selected from the group consisting of foundations and make-up bases.

17. The cosmetic composition according to claim 16, wherein said make-up cosmetic composition contains said polyethoxylated vitamin E in an amount of 0.01 to 30% by weight.

18. A cosmetic composition which provides the skin and hair with a protection against harmful oxygen species, which comprises said polyethoxylated vitamin E as claimed in claim 1 in an amount of 0.01 to 50% by weight.

19. A cosmetic composition which provides the skin and hair with protection against harmful oxygen species, which comprises said polyethoxylated vitamin E as claimed in claim 1 in combination with tocopherol or tocopheryl ester, in an amount of 0.01 to 50% by weight, and wherein the weight ratio of said polyethoxylated vitamin E to tocopherol or tocopheryl ester is 0.5:20 to 20:0.5.

20. A method for protecting the skin and hair from harmful oxygen species, which comprises applying a cosmetic composition, containing said polyethoxylated vitamin E as claimed in claim 1 in an amount of 0.01 to 50% by weight, to the skin and hair.

21. A method for protecting the skin or hair from harmful oxygen species, which comprises applying a cosmetic composition containing said polyethoxylated vitamin E as claimed in claim 1 in combination with tocopherol or tocopheryl ester, in an amount of 0.01 to 50% by weight, and wherein the weight ratio of said polyethoxylated vitamin E to tocopheryl or tocopheryl ester is 0.5:20 to 20:0.5, to the skin or hair.

* * * * *